United States Patent
Bhatia et al.

(10) Patent No.: US 11,844,772 B2
(45) Date of Patent: Dec. 19, 2023

(54) METHOD FOR TREATING RHABDOID TUMORS

(71) Applicant: Lantern Pharma Inc., Dallas, TX (US)

(72) Inventors: Kishor Bhatia, Dallas, TX (US); Aditya Kulkarni, Dallas, TX (US)

( * ) Notice: Subject to any disclaimer, the term of this patent is extended or adjusted under 35 U.S.C. 154(b) by 0 days.

(21) Appl. No.: 17/756,263

(22) PCT Filed: Dec. 29, 2021

(86) PCT No.: PCT/US2021/065441
§ 371 (c)(1),
(2) Date: May 20, 2022

(87) PCT Pub. No.: WO2022/147072
PCT Pub. Date: Jul. 7, 2022

(65) Prior Publication Data
US 2023/0321015 A1    Oct. 12, 2023

Related U.S. Application Data

(60) Provisional application No. 63/131,752, filed on Dec. 29, 2020.

(51) Int. Cl.
*A61K 31/17*    (2006.01)
*A61K 31/337*    (2006.01)
*A61K 33/243*    (2019.01)
*A61P 35/00*    (2006.01)

(52) U.S. Cl.
CPC .......... *A61K 31/17* (2013.01); *A61K 31/337* (2013.01); *A61K 33/243* (2019.01); *A61P 35/00* (2018.01)

(58) Field of Classification Search
CPC ....... A61P 35/00; A61K 31/17; A61K 31/337; A61K 33/243
See application file for complete search history.

(56) References Cited

U.S. PATENT DOCUMENTS

2008/0306147 A1  12/2008  McMorris et al.
2014/0179618 A1  6/2014  Nuber

FOREIGN PATENT DOCUMENTS

WO        2020051222        3/2020
WO   WO 2020/051222    *   3/2020    ........... A61K 31/122

OTHER PUBLICATIONS

International Search Report, dated May 4, 2022, from corresponding International Application No. PCT/US2021/065441.
Written Opinion of the International Searching Authority, dated May 4, 2022, from corresponding International Application No. PCT/US2021/065441.
Delbove, J et al.; Identification of a core member of the SWI/SNF complex, BAF165/SMARCC1, as a human tumor suppressor gene. Epigenelics. Dec. 2011, vol. 6, No. 12; p. 1444; abstract; p. 1444, 1st col. 2nd paragraph and 2nd col. 1st paragraph; DOI: 10.4161/epi.6.12.18492.
Roberts, CWM et al.; The role of SMARCB1/INI1 in development of rhabdoid tumor. Cancer Biology and Therapy. Epub Mar. 29, 2009, vol. 8, No. 5; pp. 412-415; entire document; DOI: 10.4161/cbt.8.5.8019.

\* cited by examiner

*Primary Examiner* — Erich A Leeser
(74) *Attorney, Agent, or Firm* — Greenberg Traurig, LLP; Nigamnarayan Acharya

(57) ABSTRACT

The methods include treating atypical teratoid/rhabdoid tumor by administration of HydroxyUreaMethyl Acylfulvene. Some embodiments relate to treatment of atypical teratoid/rhabdoid tumor by administration of HydroxyUreaMethyl Acylfulvene to a population or subject expressing SMARCB1.

20 Claims, 3 Drawing Sheets
Specification includes a Sequence Listing.

SEQUENCE LISTING

<160> NUMBER OF SEQ ID NOS: 4

<210> SEQ ID NO 1
<211> LENGTH: 385
<212> TYPE: PRT
<213> ORGANISM: Homo Sapiens

<400> SEQUENCE: 1

```
Met Met Met Met Ala Leu Ser Lys Thr Phe Gly Gln Lys Pro Val Lys
1               5                  10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
            85                  90                  95

Glu Glu Ile Leu Asp Gly Asn Asp Glu Lys Tyr Lys Ala Val Ser Ile
```

|   |   | 100 |   |   | 105 |   |   | 110 |   |   |   |
|---|---|---|---|---|---|---|---|---|---|---|---|

Ser Thr Glu Pro Pro Thr Tyr Leu Arg Glu Gln Lys Ala Lys Arg Asn
              115                    120                    125

Ser Gln Trp Val Pro Thr Leu Pro Asn Ser Ser His His Leu Asp Ala
    130                    135                    140

Val Pro Cys Ser Thr Thr Ile Asn Arg Asn Arg Met Gly Arg Asp Lys
145                    150                    155                    160

Lys Arg Thr Phe Pro Leu Cys Phe Asp Asp His Asp Pro Ala Val Ile
              165                    170                    175

His Glu Asn Ala Ser Gln Pro Glu Val Leu Val Pro Ile Arg Leu Asp
        180                    185                    190

Met Glu Ile Asp Gly Gln Lys Leu Arg Asp Ala Phe Thr Trp Asn Met
    195                    200                    205

Asn Glu Lys Leu Met Thr Pro Glu Met Phe Ser Glu Ile Leu Cys Asp
210                    215                    220

Asp Leu Asp Leu Asn Pro Leu Thr Phe Val Pro Ala Ile Ala Ser Ala
225                    230                    235                    240

Ile Arg Gln Gln Ile Glu Ser Tyr Pro Thr Asp Ser Ile Leu Glu Asp
              245                    250                    255

Gln Ser Asp Gln Arg Val Ile Ile Lys Leu Asn Ile His Val Gly Asn
        260                    265                    270

Ile Ser Leu Val Asp Gln Phe Glu Trp Asp Met Ser Glu Lys Glu Asn
    275                    280                    285

Ser Pro Glu Lys Phe Ala Leu Lys Leu Cys Ser Glu Leu Gly Leu Gly
290                    295                    300

Gly Glu Phe Val Thr Thr Ile Ala Tyr Ser Ile Arg Gly Gln Leu Ser
305                    310                    315                    320

Trp His Gln Lys Thr Tyr Ala Phe Ser Glu Asn Pro Leu Pro Thr Val
              325                    330                    335

Glu Ile Ala Ile Arg Asn Thr Gly Asp Ala Asp Gln Trp Cys Pro Leu
        340                    345                    350

Leu Glu Thr Leu Thr Asp Ala Glu Met Glu Lys Lys Ile Arg Asp Gln
    355                    360                    365

Asp Arg Asn Thr Arg Arg Met Arg Arg Leu Ala Asn Thr Ala Pro Ala
370                    375                    380

Trp
385

<210> SEQ ID NO 2
<211> LENGTH: 1717
<212> TYPE: DNA
<213> ORGANISM: Homo Sapiens

<400> SEQUENCE: 2

```
aacgccagcg cctgcgcact gagggcggcc tggtcgtcgt ctgcggcggc ggcggcggct      60
gaggagcccg gctgaggcgc cagtacccgg cccggtccgc atttcgcctt ccggcttcgg     120
tttccctcgg cccagcacgc cccggccccg ccccagccct cctgatccct cgcagcccgg     180
ctccggccgc ccgcctctgc cgccgcaatg atgatgatgg cgctgagcaa gaccttcggg     240
cagaagcccg tgaagttcca gctggaggac gacggcgagt tctacatgat cggctccgag     300
gtgggaaact acctccgtat gttccgaggt tctctgtaca agatataccc ctcactctgg     360
aggcgactag ccactgtgga agagaggaag aaaatagttg catcgtcaca tggtaaaaaa     420
acaaaaccta acactaagga tcacggatac acgactctag ccaccagtgt gaccctgtta     480
```

-continued

```
aaagcctcgg aagtggaaga gattctggat ggcaacgatg agaagtacaa ggctgtgtcc    540
atcagcacag agccccccac ctacctcagg aacagaagg ccaagaggaa cagccagtgg     600
gtacccaccc tgcccaacag ctcccaccac ttagatgccg tgccatgctc cacaaccatc    660
aacaggaacc gcatgggccg agacaagaag agaaccttcc cctttgctt tgatgaccat     720 gacccagctg tgatccatga aacgcatct cagcccgagg tgctggtccc catccggctg     780
gacatggaga tcgatgggca aagctgcga gacgccttca cctggaacat gaatgagaag     840
ttgatgacgc ctgagatgtt ttcagaaatc ctctgtgacg atctggattt gaacccgctg    900
acgtttgtgc cagccatcgc ctctgccatc agacagcaga tcgagtccta ccccacggac    960
agcatcctgg aggaccagtc agaccagcgc gtcatcatca agctgaacat ccatgtggga   1020
aacatttccc tggtggacca gtttgagtgg acatgtcag agaaggagaa ctcaccagag    1080
aagtttgccc tgaagctgtg ctcggagctg ggttgggcg gggagtttgt caccaccatc    1140
gcatacagca tccggggaca gctgagctgg catcagaaga cctacgcctt cagcgagaac   1200
cctctgccca cagtggagat tgccatccgg aacacgggcg atgcggacca gtggtgccca   1260
ctgctggaga ctctgacaga cgctgagatg gagaagaaga tccgcgacca ggacaggaac   1320
acgaggcgga tgaggcgtct tgccaacacg gccccggcct ggtaaccagc ccatcagcac   1380
acggctccca cggagcatct cagaagattg gccgcctct cctccatctt ctggcaagga   1440
cagaggcgag gggacagccc agcgccatcc tgaggatcgg gtgggggtgg agtgggggct   1500
tccaggtggc ccttcccggc acacattcca tttgttgagc cccagtcctg cccccaccc   1560 cacccctccct accccctcccc agtctctggg gtcaggaaga aaccttattt taggttgtgt  1620
tttgtttttg tataggagcc ccaggcaggg ctagtaacag ttttaaata aaaggcaaca    1680 ggtcatgttc aatttcttca acaaaaaaaa aaaaaaa                             1717
```

<210> SEQ ID NO 3
<211> LENGTH: 376
<212> TYPE: PRT
<213> ORGANISM: Homo Sapien

<400> SEQUENCE: 3

```
Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
                20                  25                  30

Gly Asn Tyr Leu Arg Met Phe Arg Gly Ser Leu Tyr Lys Arg Tyr Pro
            35                  40                  45

Ser Leu Trp Arg Arg Leu Ala Thr Val Glu Glu Arg Lys Lys Ile Val
        50                  55                  60

Ala Ser Ser His Asp His Gly Tyr Thr Thr Leu Ala Thr Ser Val Thr
65                  70                  75                  80

Leu Leu Lys Ala Ser Glu Val Glu Glu Ile Leu Asp Gly Asn Asp Glu
                85                  90                  95

Lys Tyr Lys Ala Val Ser Ile Ser Thr Glu Pro Thr Tyr Leu Arg
            100                 105                 110

Glu Gln Lys Ala Lys Arg Asn Ser Gln Trp Val Pro Thr Leu Pro Asn
        115                 120                 125

Ser Ser His His Leu Asp Ala Val Pro Cys Ser Thr Thr Ile Asn Arg
    130                 135                 140

Asn Arg Met Gly Arg Asp Lys Lys Arg Thr Phe Pro Leu Cys Phe Asp
```

```
                145                 150                 155                 160
Asp His Asp Pro Ala Val Ile His Glu Asn Ala Ser Gln Pro Glu Val
                    165                 170                 175

Leu Val Pro Ile Arg Leu Asp Met Glu Ile Asp Gly Gln Lys Leu Arg
                180                 185                 190

Asp Ala Phe Thr Trp Asn Met Asn Glu Lys Leu Met Thr Pro Glu Met
            195                 200                 205

Phe Ser Glu Ile Leu Cys Asp Asp Leu Asp Leu Asn Pro Leu Thr Phe
        210                 215                 220

Val Pro Ala Ile Ala Ser Ala Ile Arg Gln Gln Ile Glu Ser Tyr Pro
225                 230                 235                 240

Thr Asp Ser Ile Leu Glu Asp Gln Ser Asp Gln Arg Val Ile Ile Lys
                245                 250                 255

Leu Asn Ile His Val Gly Asn Ile Ser Leu Val Asp Gln Phe Glu Trp
                260                 265                 270

Asp Met Ser Glu Lys Glu Asn Ser Pro Glu Lys Phe Ala Leu Lys Leu
            275                 280                 285

Cys Ser Glu Leu Gly Leu Gly Gly Glu Phe Val Thr Thr Ile Ala Tyr
        290                 295                 300

Ser Ile Arg Gly Gln Leu Ser Trp His Gln Lys Thr Tyr Ala Phe Ser
305                 310                 315                 320

Glu Asn Pro Leu Pro Thr Val Glu Ile Ala Ile Arg Asn Thr Gly Asp
                325                 330                 335

Ala Asp Gln Trp Cys Pro Leu Leu Glu Thr Leu Thr Asp Ala Glu Met
            340                 345                 350

Glu Lys Lys Ile Arg Asp Gln Asp Arg Asn Thr Arg Arg Met Arg Arg
        355                 360                 365

Leu Ala Asn Thr Ala Pro Ala Trp
    370                 375

<210> SEQ ID NO 4
<211> LENGTH: 1690
<212> TYPE: DNA
<213> ORGANISM: Homo Sapien

<400> SEQUENCE: 4
aacgccagcg cctgcgcact gagggcggcc tggtcgtcgt ctgcggcggc ggcggcggct      60
gaggagcccg gctgaggcgc cagtacccgg cccggtccgc atttcgcctt ccggcttcgg     120
tttccctcgg cccagcacgc cccggccccg cccagccct cctgatccct cgcagccccgg    180 ctccggccgc ccgcctctgc cgccgcaatg atgatgatgg cgctgagcaa gaccttcggg     240
cagaagcccg tgaagttcca gctggaggac gacggcgagt tctacatgat cggctccgag     300
gtgggaaact acctccgtat gttccgaggt tctctgtaca agagataccc ctcactctgg     360
aggcgactag ccactgtgga agagaggaag aaaatagttg catcgtcaca tgatcacgga     420
tacacgactc tagccaccag tgtgaccctg ttaaaagcct cggaagtgga agagattctg     480
gatggcaacg atgagaagta caaggctgtg tccatcagca cagagccccc cacctacctc     540
agggaacaga aggccaagag aacagccag tgggtaccca ccctgcccaa cagctcccac     600
cacttagatg ccgtgccatg ctccacaacc atcaacagga accgcatggg ccgagacaag     660
aagagaacct tccccctttg ctttgatgac catgacccag ctgtgatcca tgagaacgca     720
tctcagcccg aggtgctggt ccccatccg ctggacatgg agatcgatgg cagaagctg      780 cgagacgcct tcacctggaa catgaatgag aagttgatga cgcctgagat gttttcagaa     840
```

```
atcctctgtg acgatctgga tttgaacccg ctgacgtttg tgccagccat cgcctctgcc    900
atcagacagc agatcgagtc ctaccccacg gacagcatcc tggaggacca gtcagaccag    960
cgcgtcatca tcaagctgaa catccatgtg ggaaacattt ccctggtgga ccagtttgag    1020
tgggacatgt cagagaagga gaactcacca gagaagtttg ccctgaagct gtgctcggag    1080
ctggggttgg gcggggagtt tgtcaccacc atcgcataca gcatccgggg acagctgagc    1140
tggcatcaga agacctacgc cttcagcgag aaccctctgc ccacagtgga gattgccatc    1200
cggaacacgg gcgatgcgga ccagtggtgc ccactgctgg agactctgac agacgctgag    1260
atggagaaga agatccgcga ccaggacagg aacacgaggc ggatgaggcg tcttgccaac    1320
acggccccgg cctggtaacc agcccatcag cacacggctc ccacggagca tctcagaaga    1380
ttgggccgcc tctcctccat cttctggcaa ggacagaggc gagggacag cccagcgcca    1440 tcctgaggat cgggtggggg tggagtgggg gcttccaggt ggcccttccc ggcacacatt    1500
ccatttgttg agccccagtc ctgccccca cccacccctc cctacccctc cccagtctct    1560
ggggtcagga agaaaccta ttttaggttg tgttttgttt ttgtatagga gccccaggca    1620
gggctagtaa cagtttttaa ataaaaggca acaggtcatg ttcaatttct tcaacaaaaa    1680
aaaaaaaaaa                                                           1690
```

METHOD FOR TREATING RHABDOID TUMORS

CROSS-REFERENCE

This application is a national phase application of International Application No. PCT/2021/065441, filed Dec. 29, 2021, which claims the benefit of U.S. Provisional Application No. 63/131,752, filed Dec. 29, 2020, the entirety of which is incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

TECHNICAL FIELD

This application relates to the field of chemistry and oncology. More particularly, this application relates to methods for treating atypical teratoid/rhabdoid tumor tumor using HydroxyUreaMethyl Acylfulvene.

BACKGROUND

Rhabdoid tumor (RT) is an aggressive pediatric soft tissue sarcoma that arises in the kidney, the liver, the peripheral nerves and all miscellaneous soft parts throughout the body. RI involving the central nervous system (CNS) is called atypical teratoid rhabdoid tumor. Atypical teratoid/rhabdoid tumor (AT/RT) of the CNS is an extremely rare and aggressive tumor of early childhood. The poor outcome with conventional infant brain tumor therapy has resulted in a lack of clear treatment guidelines.

Central nervous system AT/RTs typically demonstrate a variety of primitive neuroectodermal, epithelial or mesenchymal cells, which underlies the difficulty in distinguishing these tumors from other primitive neuroectodermal tumors or choroid plexus carcinomas. Immunohistochemistry is often used in the differential diagnosis, based on the typical expression of smooth muscle actin, epithelial membrane antigen and vimentin.

The vast majority of rhabdoid tumors contain hi-allelic inactivating mutations in the SMARCB1 gene. Lack of expression of the SMARCB1 protein is also employed as a specific means of distinguishing rhabdoid tumors from other malignancies with similar histologic features, especially for diagnosis of AT/RT versus primitive neuroectodermal tumors. Individuals with germline alterations of SMARCB1 are predisposed to rhabdoid tumors of the brain, kidney and soft tissues and may present with more than one primary tumor. These children are most often diagnosed within the first year of life and tend to have a worse prognosis. It is not known whether the poor prognosis is related to the presence of a germline mutation in ail of their cells, or the fact that they develop multiple and progressive primary tumors that are resistant to therapy.

The name SMARCB1 (SWI/SNF related, Matrix associated, Actin dependent Regulator of Chromatin, subfamily B, member 1) is derived from its role as a core member of the SWI/SNF chromatin remodeling complex. SMARCB1 is a core subunit present in ali variants of the SWI/SNF complex. The protein is highly conserved, as evidenced by an identical amino acid sequence in mice and humans. However, the function of SMARCB1 is poorly understood. There are no SMARCB1 paralogs and the protein lacks particularly informative protein motifs.

Accordingly, there is a need for therapies for the treatment of cancers such as rhabdoid tumors, as well as method for selecting an effective treatment regime in cancer patients.

BRIEF SUMMARY

Provided herein are methods for treatment of cancer in a subject in need thereof comprising administering to the patient a therapeutically effective amount of HydroxyUreaMethyl Acylfulvene. Provided herein are methods for treatment of cancer, wherein the cancer is an atypical teratoid rhabdoid tumor (AT/RT) and/or a malignant rhabdoid tumor (MRT), an undifferentiated sarcoma with rhabdoid features, a renal medullary carcinoma, an embryonal central nervous system tumor with rhabdoid features. HydroxyUreaMethyl Acylfulvene with negative optical activity was effective in such treatments.

Provided herein are methods for treatment of cancer in a subject in need thereof comprising administering to the patient a therapeutically effective amount of HydroxyUreaMethyl Acylfulvene, wherein the cancer is associated with SWI/SNF complex (i.e., SWI/SNF mediated cancer). Further provided herein are methods for treatment of cancer in a subject in need thereof comprising administering to the patient a therapeutically effective amount of HydroxyUreaMethyl Acylfulvene, wherein the cancer is associated with reduced expression of SWI/SNF complex. Further provided herein are methods for treatment of cancer in a subject in need thereof comprising administering to the patient a therapeutically effective amount of HydroxyUreaMethyl Acylfulvene, wherein the cancer is associated with loss of function of SWIUSNF complex. Further provided herein are methods and compositions which treat, alleviate, prevent, diminish or otherwise ameliorate the symptoms of cancer associated with the SWI/SNF complex.

Provided herein are methods for treatment of cancer in a subject in need thereof comprising administering to the patient a therapeutically effective amount of HydroxyUreaMethyl Acylfulvene, wherein the cancer is a SMARCB1 deficient cancer. SMARCB1 protein is non-functional if it is not in the nucleus. Accordingly, SMARCB1 deficient cancers are characterized by a lack of SMARCB1 protein in cell nuclei. In other words, SMARCB1 protein is not present in the cell nuclei of SMARCB1 deficient cancer cells. SMARCB1 deficiency may be caused by a number of mechanisms, In some instances, SMARCB1 may be found in the cell cytoplasm, but not the cell nucleus. SMARCB1 deficiency may be because the SMARCB1 protein itself is not expressed, or because a SMARCB1 mutant is expressed which does not localize to the nucleus, for example. Another reason for SMARCB1 deficiency may be because there is a defect in the mechanism which incorporates it into the SWI/SNF (SWItch/Sucrose Non-Fermentable) complex.

Provided herein are methods for treatment of cancer in a subject in need thereof comprising administering to the patient a therapeutically effective amount of HydroxyUreaMethyl Acylfulvene, wherein the cancer is associated with a mutation in a sequence selected from the group of sequences set forth in consisting of SEQ ID NO:1, SEQ ID NO:2, SEQ ID NO:3, and SEQ ID NO:4.

Provided herein are methods for determining sensitivity of a cancer to HydroxyUreaMethyl Acylfulvene, comprising determining an expression level of SMARCB1 gene. Further provided herein are methods, wherein a reduced expression or transcription level compared to a standard or control sample indicates a sensitivity of the cancer to HydroxyUreaMethyl Acylfulvene. Further provided herein are methods for determining sensitivity of a cancer to HydroxyUreaMethyl Acylfulvene, comprising determining an expression level of SMARCB1 protein.

Provided herein are methods for treatment of cancer in a subject in need thereof comprising administering to the patient a therapeutically effective amount of HydroxyUreaMethyl Acylfulvene, wherein the subject is assessed to have established that the cancer is associated with cells in which functional activity of SMARCB1 is low or absent. The patient may have or be suspected of having an atypical teratoid rhabdoid tumor (AT/RT) and/or a malignant rhabdoid tumor (MRT), an undifferentiated sarcoma with rhabdoid features, a renal medullary carcinoma, an embryonal central nervous system tumor with rhabdoid features.

Provided herein are methods for treating or alleviating a symptom of cancer in a subject, the method comprising: (a) determining the expression of SMARCB1 gene in a sample obtained from the subject; (b) selecting the subject having a decreased expression level of SMARCB1 gene in step a; and (c) administering to the subject selected in step b an effective amount of HydroxyUreaMethyl Acylfulvene, thereby treating or alleviating a symptom of cancer in the subject. Further provided herein are methods for treating or alleviating a symptom of cancer in a subject; the method comprising: (a) determining the expression of SMARCB1 protein in a sample obtained from the subject; (b) selecting the subject having a decreased expression level of SMARCB1 protein in step a; and (c) administering to the subject selected in step b an effective amount of HydroxyUreaMethyl Acylfulvene, thereby treating or alleviating a symptom of cancer in the subject.

Provided herein are methods for treating, or alleviating cancer in a subject in need thereof, the method comprising: (a) determining whether the cancer present in the subject is associated with cells in which the functional activity of SMARCB1 is low or absent; and (b) where the cancer is found. in step (a) to be associated with cells in which the functional activity of SMARCB1 is low or absent, administering to the patient a therapeutically effective amount of HydroxyUreaMethyl Acylfulvene:.

Provided herein are kits, for use in determining sensitivity of a specimen to HydroxyUreaMethyl Acylfulvene according to any of the method described herein, wherein the kit comprises one or more reagents, standards, and instructions for use thereof, wherein the standards comprise expression or transcription of SMARCB1, providing a threshold level, or a target level for screening sensitivity of the specimen to the HydroxyUreaMethyl Acylfulvene.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DEFINITIONS

Figure 1:
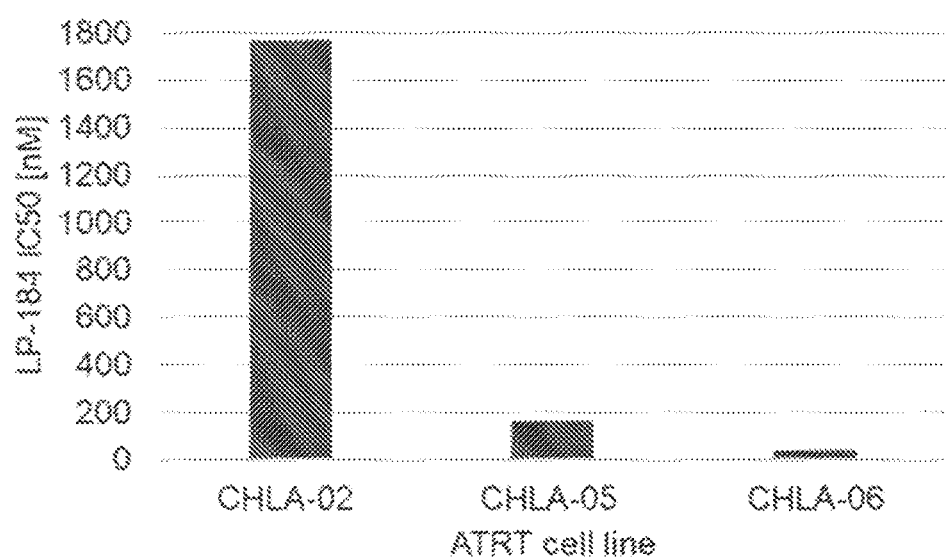
FIG. 1 shows LP-184 sensitivity in a panel of 3 ATRT cell lines.

Unless defined otherwise, all technical and scientific terms used herein have the same meaning as is commonly understood by one of skill in the art to which the subject matter herein belongs. As used herein, the following definitions are supplied in order to facilitate the understanding of the present invention.

As used herein, the terms "patient," "subject," "individual," and "host" refer to either a human or a non-human animal suffering from or suspected of suffering from a disease or disorder associated with aberrant biological or cell growth activity, The term "atypical teratoid/rhabdoid tumor" can refer to the aggressive type of rhabdoid tumor inhumans, which can be marked by alterations and deletions in the gene SMARCB1. Rhabdoid tumors/malignant rhabdoid tumors (RTs) and atypical teratoid rhabdoid tumors (ATRTs) can be aggressive cancers of the brain, kidney, and soft tissues and are frequently metastatic. They are typically diploid and lack genomic aberrations. ATRTs are correlated with the loss of SMARCB1 (also called SNF5, INI1 or BAF47), which is a component of the SWI/SNF chromatin remodeling complex.

The terms "treat" and "treating" such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life. The terms "treatment" or "treating" rhabdoid tumors and atypical teratoid rhabdoid tumors can include arresting the development or reversing the symptom or symptoms of rhabdoid tumors and atypical teratoid rhabdoid tumors and/or an improvement in clinical outcome of the patient suffering from rhabdoid tumors and atypical teratoid rhabdoid tumors. Example of improvements in clinical outcome include longer survival time, reduction in tumor size, non-growth in tumor size, and/or lack of exacerbation in neurological symptoms. Non-limiting examples of neurological symptoms include double vision, vomiting, loss of appetite, changes in mood and personality, changes in ability to think and learn, seizures, speech difficulty, and cognitive impairment.

The term "preventing" when used in relation to a condition or disease such as cancer, refers to a reduction in the frequency of, or delay in the onset of, symptoms of the condition or disease. Thus, prevention of cancer incudes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

The terms "expression level" and "level of expression," as used herein, refer to the amount of a gene product in a cell, tissue, biological sample, organism, or patient, e.g., amounts of DNA, RNA (e.g., messenger RNA (mRNA)), or proteins corresponding to a given gene.

The term "pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "therapeutic effect" refers to a beneficial local or systemic effect in animals, particularly mammals, and more particularly humans, caused by administration of a compound or composition of the invention. The phrase "therapeutically-effective amount" means that amount of a compound or composition of the invention that is effective to treat a disease or condition caused by aberrantbiological activity at a reasonable benefit/risk ratio. In some embodiments, the therapeutically effective amount of HydroxyUreaMethyl Acylfulvene or a pharmaceutically acceptable salt thereof is selected from the group consisting of 1 mg/day, 2 mg/day, 4 mg/day, 5 mg/day, 10 mg/day, 15 mg/day, 20 mg/day, 30 mg/day, 60 mg/day, 90 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day 580 mg/day, 600 mg/day, 620 mg/day, 640 mg/day, 680 mg/day, and 720 mg/day.

The therapeutically effective amount of such substance will vary depending upon the subject and disease condition being treated, the weight and age of the subject, the severity of the disease condition, the manner of administration and the like, which can readily be determined by one of skill in the art.

SMARCB1 is SWI/SNF-related matrix-associated actin-dependent regulator of chromatin subfamily B member 1, the protein and mRNA sequences of isoform A are set forth in SEQ ID NO:1 and SEQ ID NO:2, and the protein and mRNA sequences of isoform B are set forth in SEQ ID NO:3 and SEQ ID NO:4.

By a cancer "associated with cells" in which the functional activity of SMARCB1 is low or absent, it is referred to that SMARCB1 expression in the cancer cells from the patient is low or absent at the protein and/or mRNA level. Alternatively, the cancer cells may express a mutated form of a SMARCB1 protein having reduced or absent activity (i.e. the mutations lead to loss of function of the SMARCB1 protein).

The subject may have, or is suspected of having, a cancer selected from the group consisting of epithelioid sarcomas, synovial sarcomas, undifferentiated sarcomas without rhabdoid features, extra skeletal myxoid chondrosarcomas, Ewing sarcomas, mucinous carcinomas of the pancreas, malignant peripheral nerve sheath tumors, schwannomas, familial and sporadic schwannomatosis, cribriform neuroepithelial tumors, embryonal central nervous system tumors without rhabdoid features, choroid plexus carcinomas, teratoma, primitive neuroectodermal tumors (PNET), poorly differentiated chordomas, non-hodgkin lymphoma and chronic myeloid leukemia, meningioma, glioblastoma, myoepithelial carcinoma, collecting duct carcinoma.

For example, the subject may have, or may be suspected of having, cancer. The subject may have or be suspected of having an atypical teratoid rhabdoid tumor (AT/RT) and/or a malignant rhabdoid tumor (MRT), an undifferentiated sarcoma with rhabdoid features, a renal medullary carcinoma, an embryonal central nervous system tumor with rhabdoid features.

The terms "low or absent" "functional activity" of SMARCB1, as used herein, refer to reduced or absent expression of SMARCB1 in tumor cells (for example, relative to internal positive controls in tissue samples, such as normal vessel cells; inflammatory cells, surrounding normal tissue) as assessed at the protein and/or mRINA level, as well as the presence of chromosomal aberrations or DNA mutations (e.g. deletions, missense, nonsense mutations, and the like) or epigenetic alterations (e.g. DNA methylation) that lead to a reduced or lost SMARCB1 activity. Thus, the low or absent functional activity may manifest itself at the level of the genomic DNA, mRNA, protein and/or activity (i.e. function) of SMARCB1. In general, it is contemplated that the term "low functional activity" should be understood as an activity that is less than 50% of the levels detected in noncancerous normal cells. It will be appreciated that the assessment step may be performed at any time before or even during treatment of the patient. Preferably, however, the patient is assessed prior to commencement of treatment with the inhibitor.

The assessment of the patient comprises providing a sample of cells from the patient and measuring the amount of SMARCB1 protein, and/or mRNA encoding the same, in the cells. For example, the assessment of the patient may comprise measuring the amount of SMARCB1 protein in the cells, e.g. by immunohistochemistry, immunofluorescence, Western blot analysis, an immunological assay (e.g., an ELISA or other solid phase-based immunoassay such as SPRiA or amplified ELISA so called. IMIRAMP), a protein chip assay, surface-enhanced laser desorption/ionization (SELDI), high performance liquid chromatography, mass spectrometry, chemiluminescence, nephelometry/turbometry, lateral flow or pure or polarized fluorescence or electrophoresis.

It will be appreciated that the sample of cells from the patient may be cancer cells or may be normal (non-cancerous cells). For example, the latter may be useful for detecting the presence of germline mutations associated with low or absent functional activity of SMARCB1.

Alternatively, or in addition, the assessment of the patient further may comprise measuring the amount of SMARCB1 mRNA, e.g. by quantitative PCR, Northern blot analysis, deep sequencing, SAGE, or array technologies. Alternatively, or in addition, the assessment of the patient further may comprise determining the level of SMARCB1 activity (either directly or indirectly) Such activity may be assayed indirectly, for example by determining the genomic DNA, RNA or cDNA sequence, e.g. by fluorescence in situ hybridization, comparative genomic hybridization (CGH), array CGH, other array technologies, or sequencing techniques. The sequence information may then be used to identify chromosomal aberrations or DNA mutations that lead to a reduced or lost SMARCB1 activity.

Alternatively, or in addition, the assessment of the patient further may comprise determining epigenetic alterations (e.g. DNA methylation, histone modifications), that lead to low or absent SMARCB1 gene expression e.g. by DNA methylation analyses, chromatin immunoprecipitation-based techniques, mass spectrometry, chemical reactions (e.g. bisulfite treatment). eIF2alpha phosphorylation and/or PP1 activity can be used as indirect markers of SMARCB1 activity.

However, it would be apparent to a person skilled in the art that this list of techniques is not complete, and these techniques are not the only suitable methods which may be used in the present invention for measuring the functional activity (e.g., expression) of SMARCB1.

The assessment may further comprise measuring the amount of SMARCB1 protein, mRNA encoding the same and/or other measure of functional activity (sequence) in one or more control samples of cells. Such control samples may include negative control samples (in which SMARCB1 functional activity is known to be low or absent) and/or positive control samples (in which SMARCB1 functional activity is known to be at substantial levels).

Thus, the assessment may comprise performing a biopsy to extract a sample of cancer cells from the patient, which cells can then be tested (either directly or indirectly as a primary cell culture) to determine the functional activity (e.g. expression) of SMARCB1 therein.

Alternatively, or in addition, normal tissue or cells from the patient may be used to determine the functional activity (e.g. expression) of SMARCB1 therein as germline mutations have been found in patients with familial or sporadic tumors.

However, persons of skill in the art will appreciate that the functional activity (e.g. expression) of SMARCB1 may be determined indirectly. Thus, the assessment of the patient may comprise diagnosing the type of cancer from which the patient is suffering (using conventional methods well known in the art for cancer diagnosis). This diagnosis can then be used to determine the functional activity (e.g. expression) of SMARCB1 in the cancer cells (either through the empirical knowledge of the physician or by consulting a database of gene expression and gene function in known cancer types (such as Gene expression omnibus, ArrayExpress, SAGEmap, RefExA, caArrayData Portal, GeneX, HuGEindex, TCGA databases, RCGDB, International Cancer Genome Consortium databases, Mitelman database of Chromosome Aberrations and Gene Fusions in Cancer. SKY/M-FISH&CGH database, COSMIC, TmaDB, YMD, dbEST, TMAD, GXA, SMD, Novartis Gene Expression Database, OncoMine and similar databases). Upon determining that the cancer from which the patient is suffering is associated with (cancer) cells in which the function activity (e.g. expression) of SMARCB1 is low or absent, the patient may be administered HydroxyUreaMethyl Acylfulvene as a therapeutic agent to treat the cancer.

The term "expression level" as used herein may refer to protein, RNA, or mRNA level of a particular gene of interest (for example, SMARCB1). Any methods as described herein and/or known in the art can be utilized to determine the expression level. Examples include, but are not limited to, reverse transcription and amplification assays (such as PCR, ligation RT-PCR or quantitative RT-PCT), hybridization assays, Northern blotting, dot blotting, in situ hybridization, get electrophoresis, capillary electrophoresis, column chromatography, Western blotting, immunohistochemistry, immunostaining, or mass spectrometry. Assays can be performed directly on biological samples or on protein/nucleic acids isolated from the samples. it is routine practice in the relevant art to carry out these assays. For example, the measuring step in any method described herein includes contacting the nucleic acid sample from the biological sample obtained from the subject with one or more primers that specifically hybridize to the gene of interest presented herein. Alternatively, the measuring step of any method described herein includes contacting the protein sample from the biological sample obtained from the subject with one or more antibodies that bind to the biomarker of the interest presented herein.

A decreased expression level of SMARCB1 gene can include a decrease in its expression level by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the expression level of this gene measured in a different (or previous) sample obtained from the same subject.

A "reference or baseline level/value" as used herein can be used interchangeably and is meant to be relative to a number or value derived from population studies, including without limitation, such subjects having similar age range, disease status (e.g., stage), subjects in the same or similar ethnic group, or relative to the starting sample of a subject undergoing treatment for cancer. Such reference values can be derived from statistical analyses and/or risk prediction data of populations obtained from mathematical algorithms and computed indices of cancer. Reference indices can also be constructed and used using algorithms and other methods of statistical and structural classification.

In some embodiments of the present invention, the reference or baseline value is the expression level of SMARCB1 gene in a control sample derived from one or more healthy subjects or subjects who have not been diagnosed with any cancer.

In some embodiments of the present invention, the reference or baseline value is the expression level of SMARCB1 gene in a sample obtained from the same subject prior to any cancer treatment. In other embodiments of the present invention, the reference or baseline value is the expression level of SMARCB1 gene in a sample obtained from the same subject during a cancer treatment, Alternatively, the reference or baseline value is a prior measurement of the expression level of SMARCB1 gene in a previously obtained sample from the same subject or from a subject having similar age range, disease status (e.g., stage) to the tested subject.

As used herein, the phrase "a cancer found to be associated with cells" in which the functional activity of SMARCB1 is low or absent refers to a cancer comprising cells in which the functional activity of SMARCB1 is likely to be low or absent, or where the functionally activity of SMARCB1 in those cells have been validated to be low or absent. It follows that the cells referred to as being associated with the cancer are cancerous cells, or at least very likely to become cancerous due to the loss of function of the SMARCB1 tumor suppressor.

The term "sample" as used herein, refer to any biological sample derived from the subject, includes but is not limited to, cells, tissues samples, body fluids (including, but not limited to, mucus, blood, plasma, serum, urine, saliva, and semen), tumor cells, and tumor tissues. Samples can be provided by the subject under treatment or testing, Alternatively, samples can be obtained by the physician according to routine practice in the art.

The term "sensitivity," "responsive" and "responsiveness," as used herein, refer to the likelihood that a cancer treatment (e.g., LP184) has (e.g., induces) a desired effect, or, alternatively, refer to the strength of a desired effect caused or induced by the treatment in a cell (e.g., a cancer cell), a tissue (e.g., a tumor), or a patient having cancer (e.g., a human having cancer). For example, the desired effect can include inhibition of the growth of a cancer cell in vitro by more than 10%, 20%, 30%, 40%, 50%, 60%, 70%, 80%, 90%, or 100% relative to the growth of a cancer cell not exposed to the treatment. The desired effect can also include reduction in tumor mass by, e.g., about 10%, 20%, 30%, 40%, 50%, 60%, 70%, 80%, 90%, or 100%. Sensitivity to treatment may be determined by a cell proliferation assay, e.g., a cell-based assay, which measures the growth of treated cells as a function of the absorbance of the cells of an incident light beam., such as the NCI60 assays described herein. In this assay, lesser absorbance indicates lesser cell growth, and thus, sensitivity to the treatment. A greater reduction in growth indicates more sensitivity to the treatment.

The term "mutation," as used herein, means or may refer to one or more changes to the sequence of a DNA sequence or a protein amino acid sequence relative to a reference sequence, usually a wild-type sequence. A mutation in a DNA sequence may or may not result in a corresponding change to the amino acid sequence of the encoded protein. A mutation may be a point mutation, i.e. an exchange of a single nucleotide and/or amino acid for another. Point mutations that occur within the protein-coding region of a gene's DNA sequence may be classified as a silent mutation (coding for the same amino acid), a missense mutation (coding for a different amino acid), and a nonsense mutation (coding for a stop which can truncate the protein). A mutation may also be an insertion, i.e. an addition of one or more extra nucleotides and/or amino acids into the sequence. Insertions in the coding region of a gene may alter splicing of the mRNA (splice site mutation), or cause a shift in the reading frame (frameshift), both of which can significantly alter the gene product. A mutation may also be a deletion, i.e. removal of one or more nucleotides and/or amino acids from the sequence. Deletions in the coding region of a gene may alter the splicing and/or reading frame of the gene. A mutation may be spontaneous, induced, naturally occurring, or genetically engineered.

For example, the subject may have, or may be suspected of having, breast cancer. The subject may have or be suspected of having an atypical teratoid rhabdoid tumor (AT/RT) and/or a malignant rhabdoid tumor (MRT), an undifferentiated sarcoma with rhabdoid features, a renal medullary carcinoma, an embryonal central nervous system tumor with rhabdoid features.

DETAILED DESCRIPTION

HydroxyUreaMethyl Acylfulvene (currently, termed as LP-184 by Lantern Pharma, Inc.) is a semisynthetic or synthetic antitumor agent derived from the mushroom toxin illudin. S-HydroxyUreaMethyl Acylfulvene has shown promising clinical activity in certain rhabdoid tumors or cancer. HydroxyUreaMethyl Acylfulvene with negative optical activity was more effective in such treatments of AT/RT.

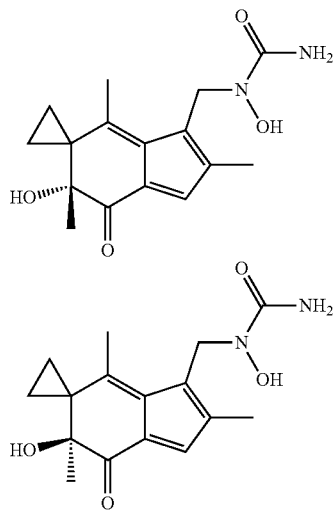

Specific embodiments relate to methods of treating atypical teratoid rhabdoid tumors or cancer, the methods including the administration of an effective amount of HydroxyUreaMethyl Acylfulvene to a subject in need thereof In some embodiments, the tumors or cancer may be from metastatic atypical teratoid rhabdoid. In one example, HydroxyUreaMethyl Acylfulvene can be administered as a monotherapy. HydroxyUreaMethyl Acylfulvene with negative optical activity was effective in such treatments.

One embodiment includes co-administering HydroxyUreaMethyl Acylfulvene and an additional therapeutic agent in separate compositions or the same composition. Thus, some embodiments include a first pharmaceutical composition comprising: (a) a safe and therapeutically effective amount of HydroxyUreaMethyl Acylfulvene or pharmaceutically acceptable salts thereof and (b) a second pharmaceutical composition. In some embodiments, the method described herein can further include subjecting the subject to a radiation therapy. In some embodiments, the radiation therapy can be a whole-organ irradiation, fractionated radiotherapy, or radiosurgery.

Some embodiments relate to a method of inhibiting proliferation of a rhabdoid tumor cell, the method including contacting the atypical teratoid rhabdoid tumors or tumor cell with HydroxyUreaMethyl Acylfulvene. In some embodiments, the contacting comprises administering an effective amount of HydroxyUreaMethyl Acylfulvene to a subject having the tumor cell. In some embodiments, the tumor is atypical teratoid rhabdoid. In some embodiments, the method can be used to treat soft tissue tumors.

The tumors with SMARCB1 (INT1) deletion or alterations of SMARCB1 can include tumors defined histologically as atypical teratoid rhabdoid tumors with locations in the CNS, peripheral nerve roots, kidneys, head and neck, paravertebral muscles, liver, mediastinum, retroperitoneum, bladder, pelvis, heart, scrotum, and subcutis. Also included for treatment with Hydroxyurea Methyl Acylfulvene are other tumors with deletion or alteration of SMARCB1. These include tumors histologically defined as epithelioid sarcomas with and sinonasal sarcomas with deletion of SMARCB1. Other tumors with SMARCB1 deletion could also include cribriform neuroepithelial tumor of the ventricle, renal medullary carcinoma and a subset of collecting duct carcinoma, epithelioid sarcoma, subsets of miscellaneous benign and malignant soft tissue tumors, and rare rhabdoid carcinoma variants of gastroenteropancreatic, and genitourinary tract origin.

Some embodiments relate to a method of inducing apoptosis in a tumor cell, the method including contacting the tumor cell with HydroxyUreaMethyl Acylfulvene. In some embodiments, the contacting comprises administering an effective amount of HydroxyUreaMethyl Acylfulvene to a subject having the tumor cell. In some embodiments, the brain tumor is atypical teratoid rhabdoid tumors or RTs.

The administration period can be a multi-week treatment cycle as long as the tumor remains under control and the regimen is clinically tolerated. In some embodiments, a single dosage of HydroxyUreaMethyl Acylfulvene or other therapeutic agent can be administered once a week, and preferably once on each of day 1 and day 8 of a three-week (21 day) treatment cycle. In some embodiments, a single dosage of HydroxyUreaMethyl Acylfulvene or other therapeutic agent can be administered once a week, twice a week, three times per week, four times per week, five times per week, six times per week, or daily during a one-week, two-week, three-week, four-week, or five-week treatment cycle. The administration can be on the same or different day of each week in the treatment cycle.

Another embodiment includes a method of treating atypical teratoid rhabdoid tumors or cancer in a subject, comprising: (a) obtaining or having obtained an expression level of the protein by immunohistochemistry, or RNA or the loss of coding regions by FISH, or DNA sequencing in a sample from a subject for a plurality of targets, wherein the plurality of targets comprises (1) SMARCB1 deletions or alteration; (b) determining that the subject is sensitive to a treatment with a HydroxyUreaMethyl Acylfulvene; and (c) administering a cancer treatment including a HydroxyUreaMethyl Acylfulvene.

HydroxyUreaMethyl Acylfulvene for use in accordance with the present invention can be mainly administered by parenteral administration, specifically including subcutaneous administration, intramuscular administration, intravenous administration, transcutaneous administration, intrathecal administration, epidural administration, intra joint administration and local administration, or may also be administered in various dosage forms, for example by oral administration if possible.

The injections for parenteral administration include for example sterile, aqueous or non-aqueous solutions, suspensions and emulsions. The aqueous solutions and suspensions include for example distilled water for injections and physiological saline. The non-aqueous solutions and suspensions include for example propylene glycol, polyethylene glycol, vegetable oils such as olive oil, alcohols such as ethanol, and Polysorbate 80 (under trade name). Such composition may contain auxiliary agents such as preservatives, moistening agents, emulsifying agents, dispersing agents, stabilizers (for example, lactose) and dissolution auxiliary agents (for example, meglumine). These are sterilized by filtering through bacteria-retaining filters, blending sterilizing agents, or irradiation. Alternatively, these may be produced once into a sterile solid composition and then dissolved or suspended in sterile water or sterile solvents for injections, prior to use.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery methodn some embodiments, the tumor can be selected from tumors having SMARCB1 (INI1) deletions or alterations including tumors defined histologically as atypical teratoid rhabdoid tumors with locations in the CNS, peripheral nerve roots, kidneys, head and neck, paravertebral muscles, liver, mediastinum, retroperitoneum, bladder, pelvis, heart, scrotum, and subcutis. Other tumors include histologically defined as epithelioid sarcomas with deletion or alteration of SMARCB1 and sinonasal sarcomas with deletion of SMARCB1. Other tumors include cribriform neuroepithelial tumor of the ventricle, renal medullary carcinoma and a subset of collecting duct carcinoma, epithelioid sarcoma, subsets of miscellaneous benign and malignant soft tissue tumors, and rare rhabdoid carcinoma variants of gastroenteropancreatic, and genitourinary tract origin.

In yet another embodiment, a method for treating an atypical teratoid/rhabdoid tumor in a patient in need thereof who has previously been treated for the prostate cancer, the method includes measuring, in a sample obtained from the patient, expression levels of SMARCB1; prognosing the patient as having an increased likelihood of cancer recurrence or cancer-specific death after the previous treatment for the atypical teratoid/rhabdoid and before recurrence of the atypical teratoid/rhabdoid based on the test expression score exceeding a reference expression score of a reference population with the same cancer; and administering treatment to the patient, the treatment comprising administering an effective amount of HydroxyUreaMethyl Acylfulvene.

The method can include subjecting the subject to radiation therapy before, after, or during treatment with HydroxyUreaMethyl Acylfulvene.

In one embodiment, the disease to be treated or prevented by the HydroxyUreaMethyl Acylfulvene is cancer. While not being limited to a specific mechanism, in some embodiments, HydroxyUreaMethyl Acylfulvene can treat or prevent cancer by inhibiting an the chromatin remodeling complex.

The liquid composition for oral administration includes for example pharmaceutically acceptable emulsions, liquids, suspensions, syrups and elixirs and contains inert diluents for general use, for example distilled water and ethanol. The composition may contain auxiliary agents such as moistening agents and suspending agents, sweetening agents, flavoring agents, aromatic agents and preservatives, other than the inert diluents.

it should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Toxicity and therapeutic efficacy of the Compounds of the Disclosure can be determined by standard pharmaceutical procedures in cell cultures or experimental animals, e.g., for determining the maximum. tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

EXAMPLES

Example 1: Use of HydroxyUreaMethyl Acylfulvene or LP-184 in Atypical Teratoid/Rhabdoid Tumors Patients receive several types of treatment, which may include surgery, chemotherapy and radiation, but the overall 2-year survival rate remains less than 15% for children aged younger than 3 years at diagnosis. ATRTs commonly have mutations in or loss of the gene SMARCB1. Increased LP-184 sensitivity correlates with decreased expression of SMARCB1. The panel of 3 ATRT cell lines, 2 of the 3 lines show evidence of high sensitivity to HydroxyUreaMethyl Acylfulvene (having a negative optical activity) or LP-184 with IC50s for those 2 being lower than 200 nM. FIG. 1 shows LP-184 sensitivity in a panel of 3 ATRT cell lines.

| ATRT cell line (molecular/epigenetic subgroup) | LP-184(-) IC50 [nM] |
| --- | --- |
| CHLA-02 (group 1) | 1770 |
| CHLA-05 (group 1) | 162 |
| CHLA-06 (group 2A/B) | 37.4 |

Example 2: Use of LP-184 in Rhabdoid Tumors

LP-184 or HydroxyUreaMethyl Acylfulvene with a negative optical activity was tested for anti-tumor efficacy in an in vivo xenograft tumor study by Lantern Pharma. LP-184 treatment (having a negative optical activity) demonstrated anti-tumor efficacy in an animal model of atypical teratoid rhabdoid tumor (ATRT). LP-184 was administered after (treatment model) the onset of disease. CHLA06 cells were implanted subcutaneously in non-obese diabetic severe combined immunodeficiency (NOD SCID) mice, formed xenograft tumors, and were thereafter treated either with vehicle control of 95% saline/5% ethanol (N=10) or 2 mg/kg or 4 mg/kg LP-184 (N=10) administered as intravenous injections.

Figure 2:
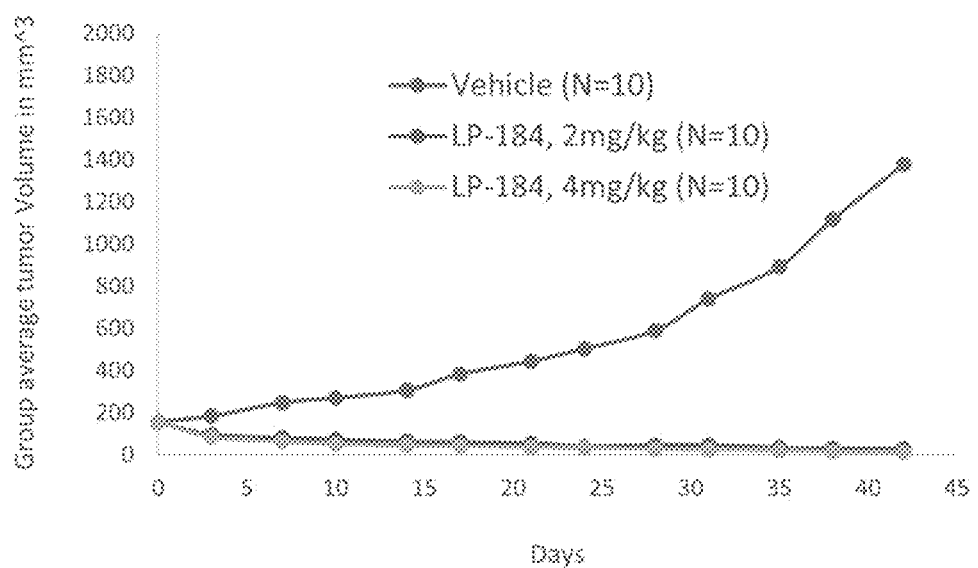
FIG. 2 shows ATRT group average tumor volume in CHLA-06 cells.

LP-184 was delivered as 5 every other day doses over 2 cycles with a break of 5 days between cycles (IV/QaDx5on/5offx2), i.e., dosing occurred on days 0, 2, 4, 6. 8, 14, 16, 18, 20, and 22 of the study. LP-184 treatment was started 4 weeks after implantation when the tumors reached a group average volume of 150 mm$^3$. On average, near complete tumor regression was observed in the LP-184 treated groups at the end of the study period on day 42. 2 out of 10 mice in the 4 mg/kg LP-184 treatment group were virtually tumor-free at study termination (tumor volume 0.5 mm$^3$). Tumor growth inhibition of 112% was observed with LP-184 treatment relative to control in this study. The final dose was delivered on day 22, and on day 40 no tumor regrowth was evident in the LP-184 treatment groups. The results are highlighted in FIG. 2, wherein the Y axis denotes tumor volume in mm$^3$ and X axis denotes days post, treatment initiation. Since tumor growth was established before administration of the anti-cancer study drug, the defining feature of the treatment tumor model, anti-tumor treatment effects may thus be appropriately attributed to LP-184.

Figure 3:
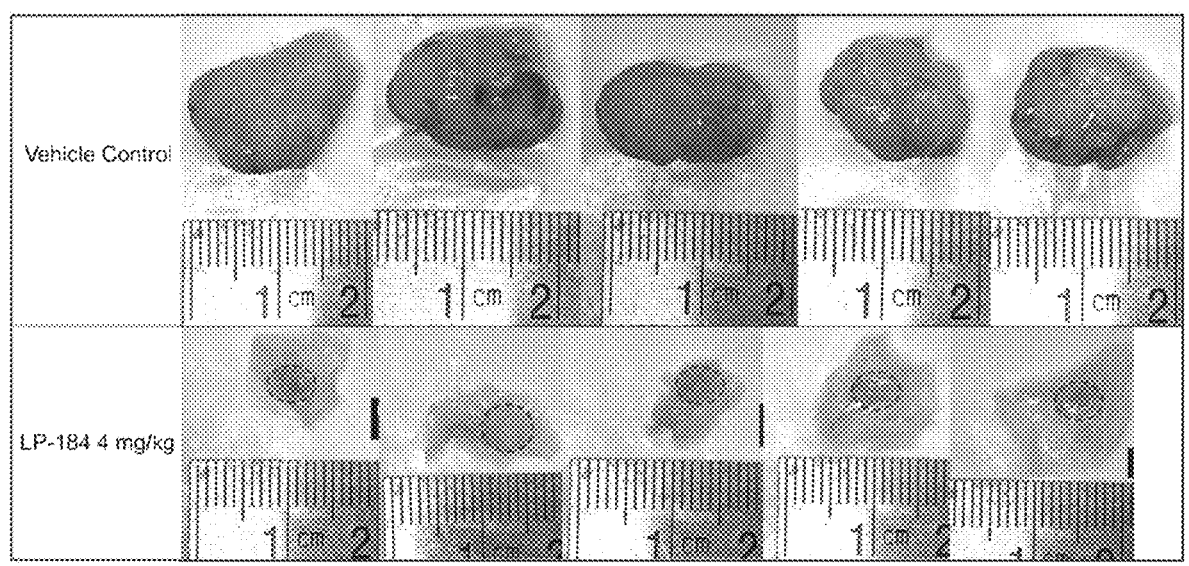
FIG. 3 shows photographs of vehicle control of CHLA06 xenograft models as compared to those treated with LP-184.

Tumor photographs taken at the end of the experiment are displayed in FIG. 3. In CHLA06 xenograft models, tumors from the vehicle control treated mice appear vividly large (length range 1.5-2 cm) whereas tumors from 4 mg/kg LP-184 treated animals shrunk remarkably (length less than 0.5 cm) or have fully regressed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

The invention claimed is:

1. A method of treating an atypical teratoid/rhabdoid tumor comprising administering an effective amount of HydroxyUreaMethyl Acylfulvene to a subject in need thereof, wherein the cancer is marked by deletions or alterations of SMARCB1 and the HydroxyUreaMethyl Acylfulvene has a negative chirality.

2. The method of claim 1, wherein the subject has a deletion or alteration of SMARCB1.

3. The method of claim 1, wherein the additional therapeutic agent is selected from the group consisting of cisplatin, paclitaxel, and other available therapies.

4. The method of claim 1, further comprising subjecting the subject to radiation therapy before, after, or during treatment with HydroxyUreaMethyl Acylfulvene.

5. The method of claim 1, wherein the radiation therapy is selected from whole-brain irradiation, fractionated radiotherapy, radio surgery, and a combination thereof.

6. The method of claim 1, wherein the subject is an animal.

7. The method of claim 1, wherein the subject or mammal is a human.

8. The method of claim 1, wherein the HydroxyUreaMethyl Acylfulvene is administered in an amount of 2 mg/kg.

9. The method of claim 1, wherein the HydroxyUreaMethyl Acylfulvene is administered in an amount of 4 mg/kg.

10. The method of claim 1, wherein administering an effective amount of HydroxyUreaMethyl Acylfulvene to a subject in need thereof results in an inhibition of the growth of cancer cells in the subject by more than 10%, 20%, 30%, 40%, 50%, 60%, 70%, 80%, 90%, or 100% relative to the growth of a cancer cell not exposed to the treatment.

11. The method of claim 1, wherein administering an effective amount of HydroxyUreaMethyl Acylfulvene to a subject in need thereof results in a reduction in tumor mass by about 10%, 20%, 30%, 40%, 50%, 60%, 70%, 80%, 90%, or 100% relative to the tumor mass not exposed to the treatment.

12. The method according to claim 1, comprising: (a) determining expression of SMARCB1 gene in a sample obtained from the subject; (b) selecting the subject having a decreased expression level of SMARCB1 gene in step a; and (c) administering to the subject selected in step b an effective amount of HydroxyUreaMethyl Acylfulvene, thereby treating or alleviating a symptom of cancer in the subject.

13. The method according to claim 1, comprising: (a) determining expression of SMARCB1 protein in a sample obtained from the subject; (b) selecting the subject having a decreased expression level of SMARCB1 protein in step a; and (c) administering to the subject selected in step b an effective amount of HydroxyUreaMethyl Acylfulvene, thereby treating or alleviating a symptom of cancer in the subject.

14. The method according to claim 1, comprising: (a) determining whether the cancer present in a patient is associated with cells in which the functional activity of SMARCB1 is low or absent; and (b) where the cancer is found in step (a) to be associated with cells in which the functional activity of SMARCB1 is low or absent, administering to the patient a therapeutically effective amount of HydroxyUreaMethyl Acylfulvene.

15. A kit, for use in determining sensitivity of a specimen to HydroxyUreaMethyl Acylfulvene according to the method of any one of claims 1, wherein the kit comprises one or more reagents, standards, and instructions for use thereof, wherein the standards comprise expression or transcription of SMARCB1, providing a threshold level, or a target level for screening sensitivity of the specimen to the HydroxyUreaMethyl Acylfulvene; and the HydroxyUreaMethyl Acylfulvene has a negative chirality.

16. The method of claim 9, wherein the cancer is associated with reduced expression of SWI/SNF complex or loss of function of SWI/SNF complex.

17. The method of claim 9, wherein the cancer is associated with reduced expression of SMARCB1 or loss of function of SMARCB1.

18. The method of claim 9, wherein the cancer is associated with a mutation in a sequence selected from the group of sequences set forth in consisting of SEQ ID NO:1, SEQ ID NO:2, SEQ ID NO:3, and SEQ ID NO:4.

19. A method for treating an atypical teratoid/rhabdoid tumor in a patient in need thereof who has previously been treated for the prostate cancer, the method comprising: measuring, in a sample obtained from the patient, expression levels of SMARCB1, prognosing the patient as having an increased likelihood of cancer recurrence or cancer-specific death after the previous treatment for the atypical teratoid/rhabdoid and before recurrence of the atypical teratoid/rhabdoid based on the test expression score exceeding a reference expression score of a reference population with the same cancer; and administering treatment to the patient, the treatment comprising administering an effective amount of HydroxyUreaMethyl Acylfulvene having a negative optical activity.

20. The method of claim 1, further comprising subjecting the subject to radiation therapy before, after, or during treatment with HydroxyUreaMethyl Acylfulvene.

\* \* \* \* \*